US012569199B2

(12) United States Patent
Golenberg et al.

(10) Patent No.: US 12,569,199 B2
(45) Date of Patent: Mar. 10, 2026

(54) SKIN ADHESIVE PATCH WITH REFRESHABLE PERIMETER, AND RELATED DEVICE ASSEMBLY

(71) Applicant: MEDTRONIC MINIMED, INC., Northridge, CA (US)

(72) Inventors: Lavie P. Golenberg, Bloomfield Hills, MI (US); Brian J. Ross, Maple Grove, MN (US); Ellis Garai, Woodland Hills, CA (US); Nicole L. Parks, Crystal, MN (US); Brian Joseph Ferry, Minneapolis, MN (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 1275 days.

(21) Appl. No.: 17/326,018

(22) Filed: May 20, 2021

(65) Prior Publication Data

US 2022/0370012 A1 Nov. 24, 2022

(51) Int. Cl.
*A61F 13/02* (2024.01)
*A61B 5/00* (2006.01)

(52) U.S. Cl.
CPC ........ *A61B 5/6833* (2013.01); *A61B 5/68335* (2017.08)

(58) Field of Classification Search
CPC .. A61F 13/0246; A61F 13/02; A61F 13/0259; A61F 13/0263; A61F 5/443; A61F 5/445; A61B 5/6801; A61B 5/6813; A61B 5/683; A61B 5/6832; A61B 5/68; A61B 5/6802
See application file for complete search history.

(56) References Cited

U.S. PATENT DOCUMENTS

| | | | | |
|---|---|---|---|---|
| 4,681,574 | A | * 7/1987 | Eastman | ................. A61F 5/443 |
| | | | | 604/344 |
| 4,755,173 | A | 7/1988 | Konopka et al. | |
| 5,264,218 | A | * 11/1993 | Rogozinski | ............ A61L 15/42 |
| | | | | 424/443 |
| 5,391,250 | A | 2/1995 | Cheney, II et al. | |
| 5,485,408 | A | 1/1996 | Blomquist | |
| 5,522,803 | A | 6/1996 | Teissen-Simony | |
| 5,665,065 | A | 9/1997 | Colman et al. | |
| 5,800,420 | A | 9/1998 | Gross et al. | |
| 5,807,375 | A | 9/1998 | Gross et al. | |
| 5,925,021 | A | 7/1999 | Castellano et al. | |

(Continued)

FOREIGN PATENT DOCUMENTS

JP 2018102576 A 7/2018

*Primary Examiner* — Camtu T Nguyen
(74) *Attorney, Agent, or Firm* — Foley & Lardner LLP

(57) ABSTRACT

An apparatus adherable to a user's skin, such as a wearable medical device, is presented here. An embodiment of the apparatus includes a durable component having a periphery defining a footprint of the durable component, and a skin adhesive component coupled to the durable component to facilitate securing the durable component to the user's skin. The skin adhesive component includes a first region and a second region removably attached to the first region. The first region of the skin adhesive component resides completely within the footprint of the durable component. After removal of the second region of the skin adhesive component, the first region remains intact and protected underlying the durable component.

20 Claims, 7 Drawing Sheets

(56)          References Cited

U.S. PATENT DOCUMENTS

| | | | |
|---|---|---|---|
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,814,720 | B2 * | 11/2004 | Olsen ..................... A61F 5/448 |
| | | | 604/339 |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,165,655 | B2 | 4/2012 | Grassl |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,174,034 | B2 * | 11/2015 | Loori .................... A61M 35/30 |
| 10,729,900 | B2 | 8/2020 | Silver et al. |
| 2004/0049146 | A1 * | 3/2004 | Kolte .................. A61F 13/0203 |
| | | | 602/61 |
| 2005/0080372 | A1 * | 4/2005 | Nielsen ............... A61F 13/0203 |
| | | | 602/42 |
| 2007/0123819 | A1 | 5/2007 | Mernoe et al. |
| 2008/0039760 | A1 | 2/2008 | Lesko |
| 2010/0160861 | A1 | 6/2010 | Causey, III et al. |
| 2013/0267790 | A1 | 10/2013 | Pfuetzner et al. |
| 2014/0323941 | A1 * | 10/2014 | Lee .......................... A61L 15/60 |
| | | | 428/137 |
| 2016/0030646 | A1 * | 2/2016 | Hartwell ............... A61M 1/915 |
| | | | 604/319 |
| 2016/0058380 | A1 | 3/2016 | Lee et al. |
| 2017/0007439 | A1 * | 1/2017 | Boksan ................... A61F 5/443 |
| 2018/0280609 | A1 | 10/2018 | Nishimura et al. |
| 2019/0216397 | A1 | 7/2019 | Yavorsky et al. |
| 2019/0336345 | A1 * | 11/2019 | Bannwart ............. A61M 1/916 |
| 2020/0085349 | A1 | 3/2020 | Bremer |
| 2020/0163792 | A1 * | 5/2020 | Schertiger ............... A61F 5/443 |
| 2020/0261643 | A1 | 8/2020 | Boyaval et al. |
| 2021/0177664 | A1 * | 6/2021 | Chan ................. A61F 13/00063 |

* cited by examiner

SKIN ADHESIVE PATCH WITH REFRESHABLE PERIMETER, AND RELATED DEVICE ASSEMBLY

TECHNICAL FIELD

The present technology is generally related to wearable devices and components, such as medical devices that are designed to be adhered to the user's skin. More particularly, the present technology is related to a wearable device assembly that includes a skin adhesive patch with a refreshable perimeter region.

BACKGROUND

Certain diseases can be monitored and treated in a continuous manner or at particular times throughout the day using medical devices that externally attach to the body. Medical devices that are connected to the body externally require a robust and stable connection that can last for one or more days of wear while providing consistent and accurate monitoring or treatment.

For example, a patient can utilize external sensor devices that connect a sensor to the body to monitor his or her condition. The connection of external sensor devices to the body must be stable to obtain accurate physiological readings of the patient. Delivery devices can also be externally connected to the body to deliver medication. The connection of external delivery devices to the body must be steady enough to allow consistent fluid-flow communication of the medication from the device to the body.

Diabetic patients can monitor their blood glucose (BG) levels and deliver insulin continuously or at certain times throughout the day utilizing external devices. A diabetic patient can measure his or her BG level using a BG measurement device to determine if treatment is needed, be it with glucose to raise glucose levels or insulin to lower glucose levels. Moreover, a diabetic patient may use a continuous glucose measurement or monitoring system to monitor sensor glucose (SG) readings throughout the day. To deliver insulin to the body, some diabetic patients use insulin delivery devices, including external infusion pumps, compact patch pump devices, and insulin delivery sets. Such monitoring and delivery devices can be affixed to the body in a stable manner using skin adhesive components.

BRIEF SUMMARY

The subject matter of this disclosure generally relates to a wearable device, such as a medical device or component that can be affixed to the skin of a user. More specifically, the subject matter of this disclosure relates to a skin adhesive component suitable for use with such a wearable device.

In one aspect, the present disclosure provides an apparatus adherable to a user's skin. An embodiment of the apparatus includes a durable component with a housing having a periphery. The apparatus also includes a skin adhesive component coupled to the durable component to facilitate securing the durable component to the user's skin. The skin adhesive component includes a first region and a second region removably attached to the first region along a boundary to define a renewable edge of the skin adhesive component. A projection of the periphery of the housing onto the skin adhesive component completely surrounds the boundary.

In another aspect, the disclosure provides an apparatus adherable to a user's skin. An embodiment of the apparatus includes: a durable component having a periphery defining a footprint of the durable component; and a skin adhesive component coupled to the durable component to facilitate securing the durable component to the user's skin. The skin adhesive component includes: a first region; and a second region removably attached to the first region. The first region of the skin adhesive component resides completely within the footprint of the durable component.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
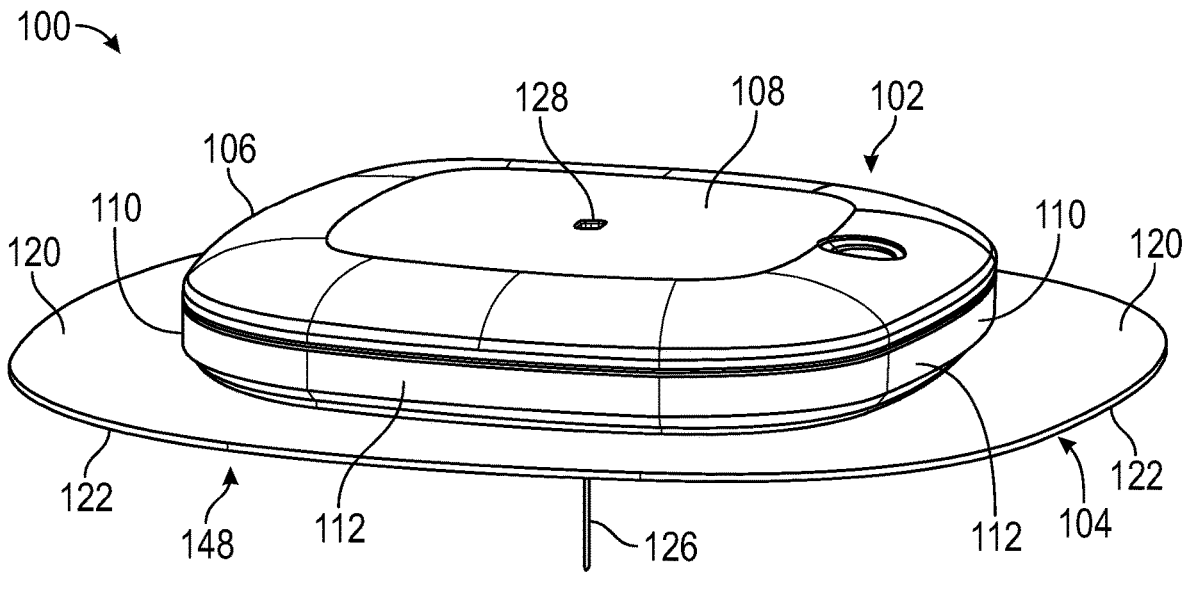
FIG. 1 is a perspective view of an exemplary embodiment of an apparatus that is adherable to a user's skin.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

Current methods of attaching devices or components to the skin or body of a user utilize adhesive layers, materials, patches, or the like. For example, a device can be coupled to a skin adhesive component, which in turn can be affixed to the user's skin. Embodiments herein are drawn to an apparatus that is adherable to a user's skin via a skin adhesive component (e.g., an adhesive patch). Over time, the exposed edges of a skin adhesive component can loosen, fray, or lift away from the skin, resulting in an undesirable appearance and potentially compromised coupling between the apparatus and the user's skin. The subject matter presented here relates to a skin adhesive component having at least one removable region, segment, or portion, e.g., an outer region. The user can separate and discard the removable region to refresh the exposed edge of the skin adhesive component, to clean up the appearance of the deployed apparatus, and to extend the effective life of the skin adhesive component.

Embodiments described herein may be utilized in conjunction with medical devices, such as wearable, portable medical devices. The medical device can be configured to provide monitoring or treatment operation on a user while attached to the body. Medical devices that can utilize various embodiments described herein include, but are not limited to, sensors, physiological characteristic monitors, and infusion medium delivery systems, which may include or cooperate with cannula or needle inserting devices. Although many different applications are possible, exemplary embodiments are used in applications that incorporate a continuous glucose monitoring (CGM) system. That said, the subject matter described herein is not limited to use with such system (or any particular configuration or realization thereof).

Devices according to embodiments herein can be used with, connectable to and disconnectable from or incorporated in a portion of a medical device system. As a non-limiting example, a needle inserting device can be connected to a base structure of an infusion delivery device for insertion of a needle, after which the needle inserting device can be removed from the base and replaced with a different device component such as, but not limited to a reservoir and pump or drive device can be coupled to the base for operation. For example, a sensor or delivery medical device and method may operate to insert a cannula or needle through a user's skin to convey a fluid from the user to one or more sensor elements and/or to provide a fluid flow path for conveying an infusion medium through a hollow channel in the cannula or needle and into the user. Embodiments can also be configured to provide a contiguous fluid-flow passage for fluid transfer between a reservoir and the user when the hollow needle or cannula is inserted in the user. For example, the user could use the device and method with infusion delivery systems. As a non-limiting example, the device can be used with any insulin infusion pump, patch, insulin infusion set and the like that is used externally on the body of a user.

In some embodiments, the medical device can include one or more components. In embodiments, at least a portion of a medical device can be adapted to be secured to the user during operation of the medical monitoring or treatment device and another portion of the medical device may be removable during operation of the device. Certain embodiments may be directed to use of the device and method with a sensor monitoring system. Such embodiments can be used with a sensor having a sensor base with a cannula that can be inserted into the skin of a user and a sensor transmitter that is connectable to and disconnectable from the sensor base while the base remains attached to the skin. The sensor can provide a signal indicative of a characteristic of a user and may be implanted in and/or through subcutaneous, dermal, sub-dermal, inter-peritoneal or peritoneal tissue. Embodiments of a surface mounted sensor could utilize interstitial fluid harvested from underneath the skin. In specific embodiments, the sensor can determine glucose levels in the blood and/or body fluids of the user. However, it will be recognized that further embodiments may be used to determine the levels of other agents, characteristics or compositions, such as hormones, cholesterol, medication concentrations, pH, oxygen saturation, viral loads (e.g., HIV), or the like. Embodiments may provide sensor readings on an intermittent or continuous basis.

The sensor can be an electrode-type sensor, or other type of sensor, such as chemical based, optical based or the like. The sensor transmitter can store and provide sensor readings to other devices or other components of a sensor system. For example, the transmitter can process and wirelessly transmit sensor signals to a remotely located data receiving device. Some embodiments can allow a user or a physician to disconnect the sensor transmitter from the sensor base to retrieve sensor readings. In other embodiments, the sensor controller and/or sensor transmitter used with the device need not be disconnected from the sensor base during operation and can be connected for the entire duration of wear. In further embodiments, the sensor base and sensor transmitter can be manufactured as one medical device instead of multiple components.

Referring now to FIG. 1, a removable apparatus 100, such as an analyte monitoring device, is illustrated. In certain embodiments, the apparatus 100 is part of a continuous glucose monitoring system. As shown, the apparatus 100 includes a durable component 102 (e.g., a sensor transmitter unit) and a skin adhesive component 104 coupled to the durable component to facilitate securing the durable component 102 to the user's skin. The durable component 102 includes a housing 106 having a top side 108 and an opposite bottom side (hidden from view in FIG. 1). The housing 106 extends to, and terminates at, a periphery 110. The periphery 110 defines a footprint of the durable component 102. In this regard, the footprint corresponds to the projection of the housing 106 onto the skin adhesive component 104, when viewed directly from above (or below) the apparatus 100— see, for example, the top views shown in FIGS. 3-10. Depending on the particular embodiment and intended application, the periphery 110 may be defined by a base section of the housing 106, a sidewall section of the housing 106, an upper lid or cap section of the housing 106, or the like. For the embodiment depicted in FIG. 1, the periphery 110 corresponds to a straight sidewall section 112 of the housing 106.

The skin adhesive component 104 serves to adhere the durable component 102 to the user's skin. In certain embodiments, the skin adhesive component 104 includes a backing material 120 (e.g., the top layer of the skin adhesive component 104) and an adhesive material 122 (e.g., the bottom layer of the skin adhesive component 104) on the backing material 120. The adhesive material 122 is the layer that makes contact with the user's skin. In typical embodiments, the adhesive material 122 is a continuous layer that extends throughout the entire area of the backing material 120. The adhesive material 122 may include, for example, a pressure sensitive adhesive such as an acrylic adhesive, although other suitable adhesives may be used. Although not shown in FIG. 1, during fabrication and assembly, the skin adhesive component 104 may include a removable liner that covers the adhesive material 122. In some implementations (e.g., where the apparatus 100 is loaded into an insertion device or mechanism that deploys the apparatus 100 onto the skin of the user), the removable liner is removed and discarded before final assembly and packaging occurs. In other implementations, the removable liner remains intact such that the user is expected to remove it before affixing the apparatus onto the skin.

In accordance with the illustrated embodiment, the apparatus 100 includes an analyte sensor 126 extending downward from the durable component 102. The housing 106 may include an opening 128 formed therein to receive a needle or probe to insert the analyte sensor 126 into the user's skin, i.e., for implantation.

Figure 2:
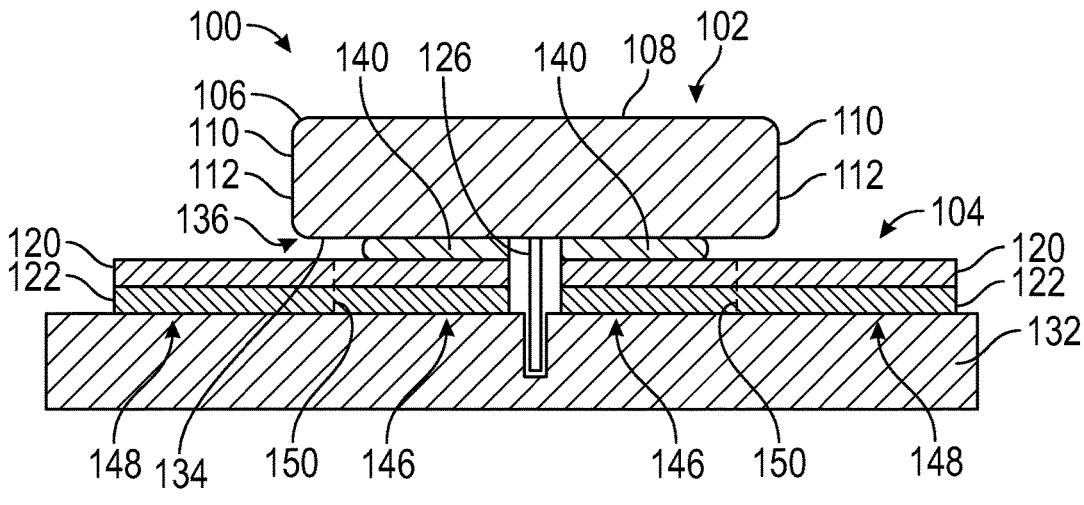
FIG. 2 is a schematic cross-sectional view of the apparatus as deployed on the user's skin.

FIG. 2 is a schematic cross-sectional view of the apparatus 100 as deployed on the user's skin 132. FIG. 2 depicts the bottom side 134 of the housing 106, which represents the termination of a base section 136 of the housing 106. For the illustrated embodiment, the footprint or periphery 110 of the housing 106 is defined by the sidewall section 112 and the base section 136 (because those features exhibit the same projection onto the skin adhesive component 104 when viewed from directly above or below the apparatus 100).

As shown in FIG. 2, the adhesive material 122 of the skin adhesive component 104 is in direct contact with, and is affixed to, the user's skin 132. Although hidden from view in FIG. 1, the apparatus 100 includes a double-sided pressure sensitive adhesive element 140 that couples the base section 136 of the durable component 102 to the backing material 120 of the skin adhesive component 104. The adhesive element 140 may include a hole formed therein to accommodate the analyte sensor 126.

In accordance with certain embodiments, the skin adhesive component 104 includes at least two regions that can be separated from each other. The illustrated embodiment of the skin adhesive component 104 includes a first region 146 and a second region 148 removably attached to the first region 146 along a boundary 150 to define a renewable edge of the skin adhesive component 104. The second region 148 is visible in FIG. 1; the first region 146 is hidden from view in FIG. 1. For this particular embodiment, a projection of the periphery 110 of the housing 106 onto the skin adhesive component 104 completely surrounds the boundary 150. In other words, the first region 146 of the skin adhesive component 104 resides completely within the footprint of the durable component 102.

Figure 3:
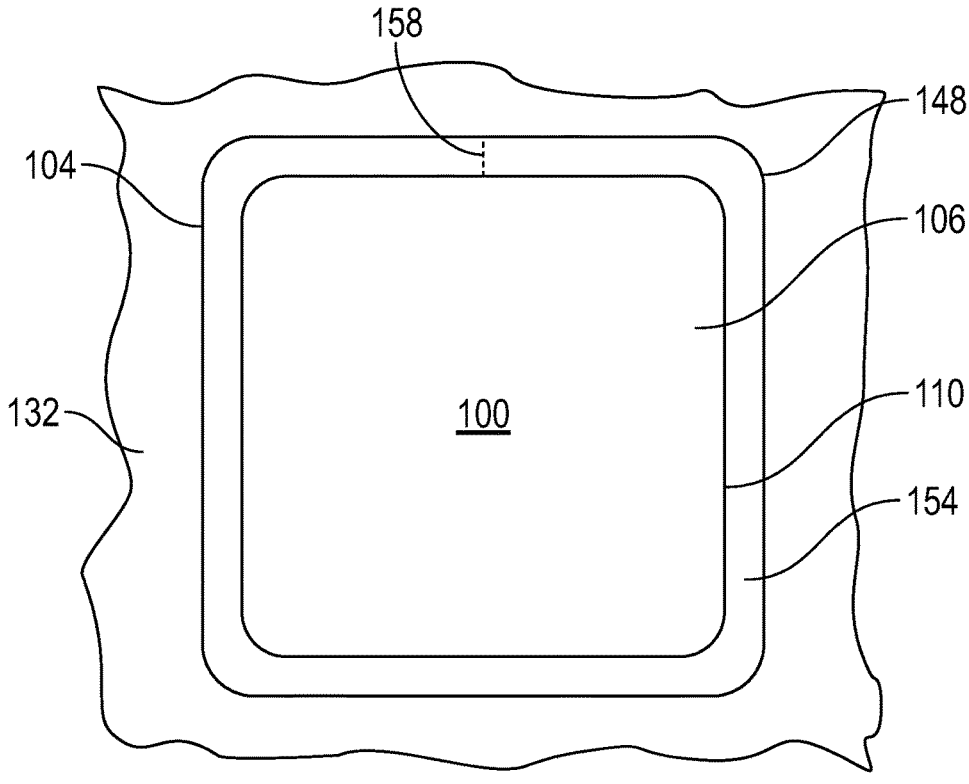
FIG. 3 is top view of the apparatus as deployed on the user's skin.
Figure 4:
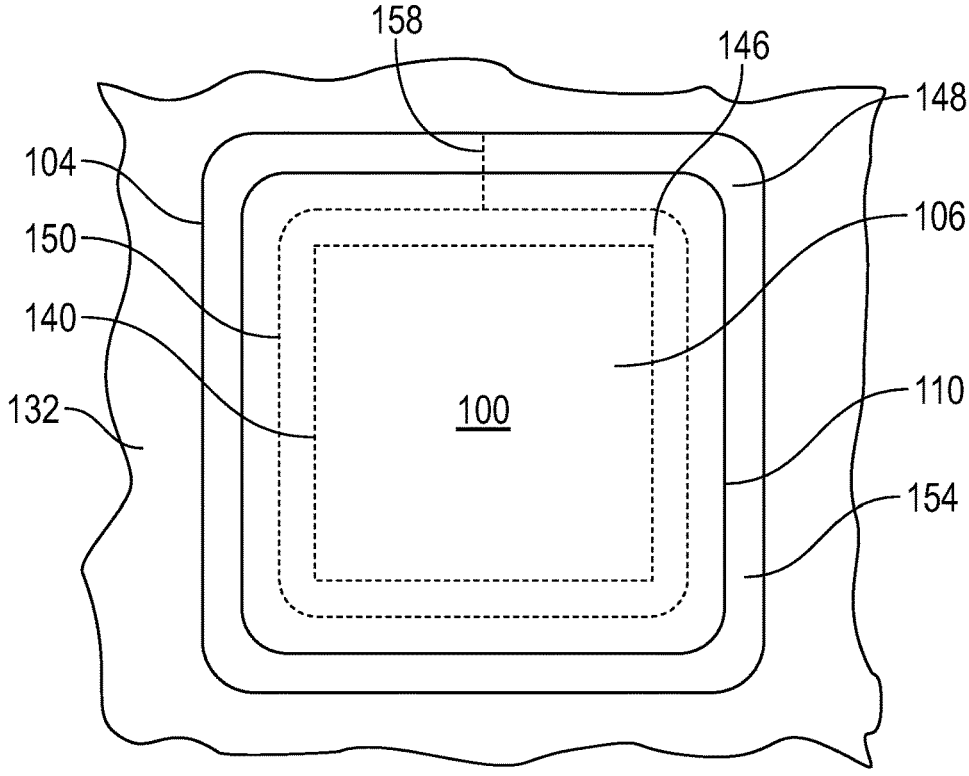
FIG. 4 is another top view of the apparatus as deployed on the user's skin, with certain hidden features depicted with phantom lines.

FIG. 3 is top view of the apparatus 100 as deployed on the user's skin 132, and FIG. 4 is another top view of the apparatus 100 as deployed on the user's skin 132, with certain hidden features depicted with phantom lines. FIG. 3 shows the outline of the housing 106, which corresponds to the periphery 110, and an exposed outer portion 154 of the second region 148 of the skin adhesive component 104. These features are also shown and labeled in FIG. 4.

FIG. 4 depicts the adhesive element 140 as a square shape in dashed lines. FIG. 4 also depicts the boundary 150 as a dashed line between the first region 146 and the second region 148. FIG. 4 shows how the projection of the periphery 110 completely surrounds the boundary 150, such that the housing 106 overlies and covers the adhesive element 140 and the boundary 150. Moreover, the projection of the boundary 150 is located between the projections of the adhesive element 140 and the periphery 110 (as viewed from the top in FIG. 4). This arrangement is also shown in FIG. 2.

In certain embodiments, the skin adhesive component 104 includes perforations formed therein to define the boundary 150. Accordingly, the dashed lines depicting the boundary 150 in FIG. 4 may correspond to a layout of perforations. Although not always required, the skin adhesive component 104 may also include a perforated slit 158, which may be continuous with the layout of perforations that define the boundary 150. FIG. 4 depicts the slit 158 extending from the boundary 150, and FIG. 3 depicts an exposed section of the slit 158. The slit 158 can be provided to make it easier to remove the second region 148 from the first region 146.

As an alternative implementation, the skin adhesive component 104 can be partially cut, slit, scored, punctured, or broken in a particular layout or pattern to define the boundary 150. Accordingly, the dashed lines that represent the boundary 150 in FIG. 4 may correspond to a cut, slit, or otherwise physically compromised pattern of the skin adhesive component 104. The slit 158 can also be realized as a fully or partially cut or slit section of the skin adhesive component 104.

As another alternative implementation, the skin adhesive component 104 may include a mechanically weakened or compromised outline to define the boundary 150. Accordingly, the dashed lines that represent the boundary 150 in FIG. 4 may correspond to a weakened outline or pattern that makes it easier to separate the second region 148 from the first region 146, while leaving the first region 146 intact. The slit 158 can also be realized as a weakened section of the skin adhesive component 104.

Figure 5:
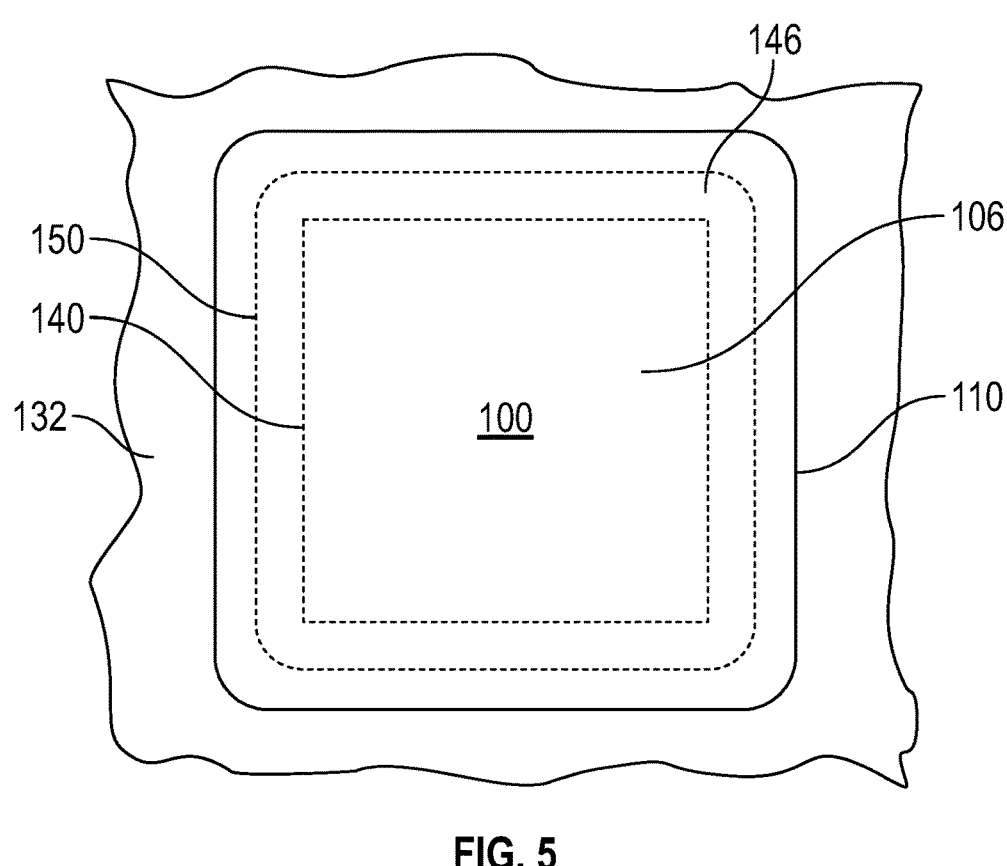
FIG. 5 is a top view of the apparatus, after removal of an outer region of a skin adhesive component.

The separable multi-part configuration of the skin adhesive component 104 provides various benefits and advantages. For example, the second region 148 can be removed at any time after the apparatus 100 has been affixed to the user's skin if a clean appearance is desired (no visible adhesive patch). As another example, the second region 148 can be easily removed if its outer edges become frayed, begin to peel away, or get dirty. Thereafter, the first region 146 remains intact underneath and physically protected by the durable component 102. FIG. 5 is a top view of the apparatus 100, after removal of the outer region of the skin adhesive component 104. As shown in FIG. 5, only the first region 146 remains, and the boundary 150 now defines a refreshed edge of what remains of the skin adhesive component 104. This refreshed edge resides completely under the periphery 110 of the apparatus 100. This arrangement can extend the wearable life of the removable apparatus 100 by protecting the first region 146 from exposure to the elements, peeling, and the like.

Figure 6:
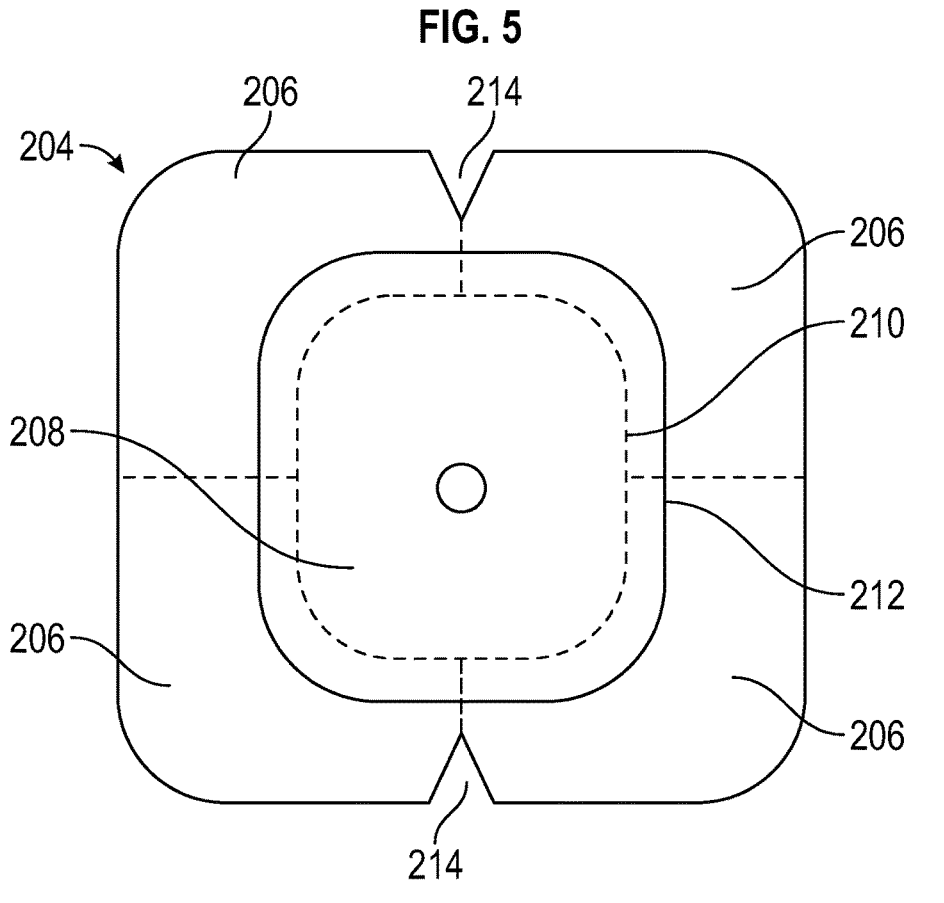
FIGS. 6-10 are schematic top views that depict exemplary embodiments of skin adhesive components suitable for use with an apparatus that is adherable to a user's skin.

FIGS. 1-5 relate to an exemplary embodiment that employs a ring shaped boundary between two regions of the skin adhesive component 104. FIG. 6 depicts another embodiment that includes a skin adhesive component 204 having a plurality of individually removable outer segments 206 surrounding an inner region 208. The perimeter of the inner region 208 is defined by a boundary 210 (e.g., a perforated outline). As described above, the boundary 210 is located inside the periphery 212 of the durable component that is affixed to the skin adhesive component 204. For this embodiment, the outer segments 206 can be removed (individually or in combination) at any time as desired by the user. Any number of notches 214, slits, or cuts can be formed in the skin adhesive component 204 to facilitate removal of the outer segments 206. Although the skin adhesive component 204 includes four removable outer segments 206 and one inner region 208 (for a total of five regions), more or less than five can be utilized.

Figure 7:
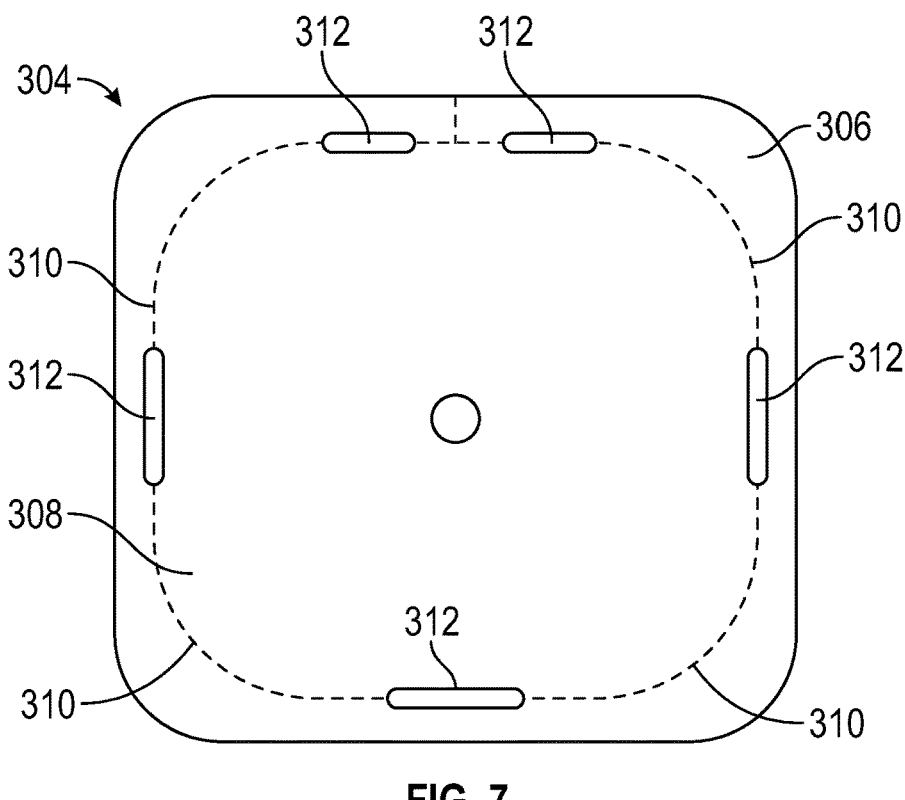

FIG. 7 depicts another embodiment that includes a skin adhesive component 304 having a removable outer region 306 surrounding an inner region 308. The perimeter of the inner region 208 is at least partly defined by a boundary 310 (e.g., a perforated outline). The skin adhesive component 304 also includes one or more through hole cutouts 312 along the boundary 310. The cutouts 312 make it easier for the user to remove the outer region 306. Moreover, the cutouts 312 provide the additional benefit of helping with the breathability of the skin adhesive component 304. As described above, after removal of the outer region 306, the refreshed outer edge of the skin adhesive component 304 (e.g., the boundary 310) will be protected underneath the durable component that is affixed to the skin adhesive component 304.

Figure 8:
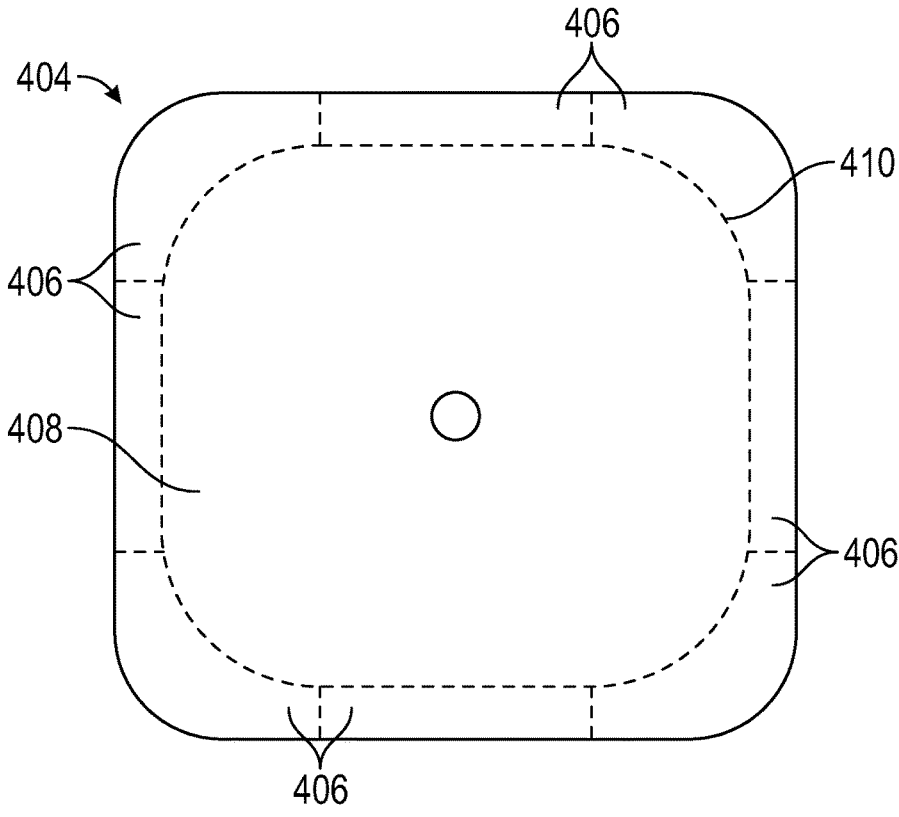

FIG. 8 depicts another embodiment that includes a skin adhesive component 404 having eight independently removable outer segments 406 surrounding an inner region 408. The perimeter of the inner region 408 is defined by a boundary 410 (e.g., a perforated outline). As described above, after removal of the outer segments 406, the refreshed outer edge of the skin adhesive component 404 (e.g., the boundary 410) will be protected underneath the durable component that is affixed to the skin adhesive component 404. Although the skin adhesive component 404 includes a total of nine regions, more or less than nine can be utilized.

Figures 9, 10:
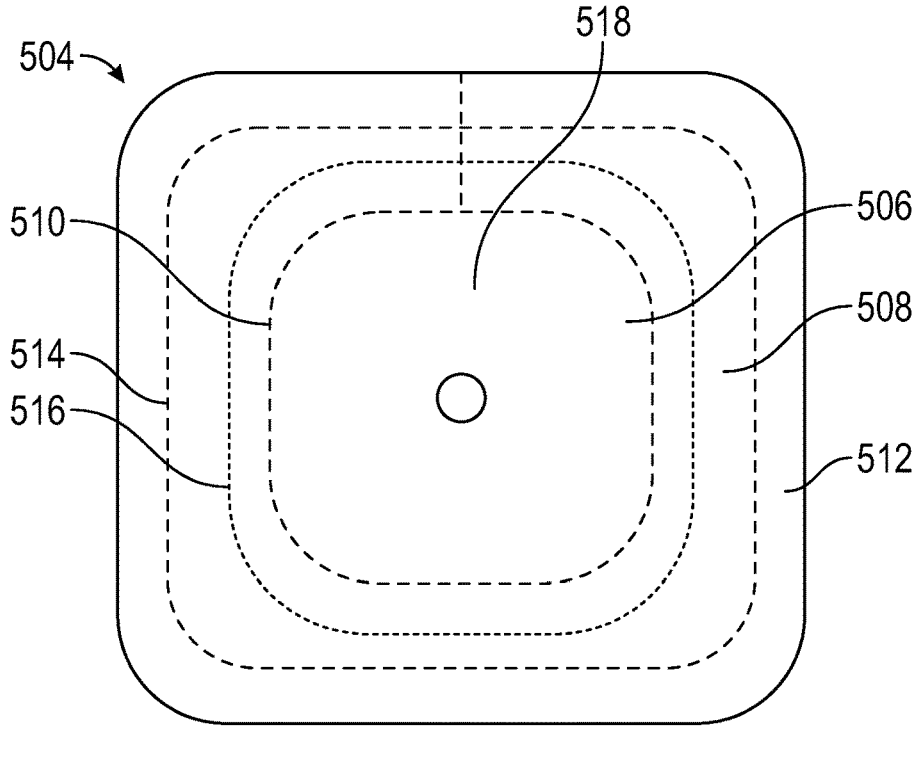

FIG. 9 depicts another embodiment that includes a skin adhesive component 504 having a first (inner) region 506, a second (intermediate) region 508 removably attached to the first region 506 along a first boundary 510, and a third (outer) region 512 removably attached to the second region 508 along a second boundary 514. The skin adhesive component 504 is similar to the skin adhesive component 104 described previously, with the addition of the third region 512 surrounding the second region 508. Thus, the first boundary 510 represents a first renewable edge of the skin adhesive component 504, and the second boundary 514 defines a second renewable edge of the skin adhesive component 504. For this embodiment, the second boundary 514 resides outside of the periphery 516 of the durable component 518 that is affixed to the skin adhesive component 504. The first boundary 510 is located inside of the periphery 516, such that the first region 506 remains protected by the durable component 518 after removal of the third region 512 and the second region 508.

FIG. 10 depicts another embodiment that includes a skin adhesive component 604 having a first (inner) region 606 and a second (outer) region 608 removably attached to the first region 606 along a spiral shaped boundary 610. The innermost section of the boundary 610 defines a renewable edge of the skin adhesive component 604. The user can initiate removal of the second region 608 at an outer flap or tab area 612 and peel away the spiral shaped section until all that remains is the first region 606. This configuration can improve user comfort because only a small surface area of the skin adhesive component 604 is peeled away as the spiral shaped segment unwinds. As described above, after removal of the second region 608, the refreshed outer edge of the skin adhesive component 604 (e.g., the newly defined outer perimeter of the first region 606) will be protected underneath the durable component that is affixed to the skin adhesive component 604. Although the skin adhesive component 604 includes one spiral shaped segment, an embodiment can include more than one spiral segment connected in series and/or connected outside of the first spiral shaped segment.

FIGS. 1-10 generally depict various embodiments that use a substantially rectangular shaped skin adhesive component to accommodate a substantially rectangular durable component. It should be appreciated that the skin adhesive component and the boundary (or boundaries) between removable segments of the skin adhesive component can be shaped, sized, and configured in alternative ways to accommodate the particular design and configuration of the durable component. For example, the skin adhesive component and the removable segment boundary may instead be substantially triangular in shape, substantially circular in shape, substantially elliptical in shape, or the like.

Figure 11:
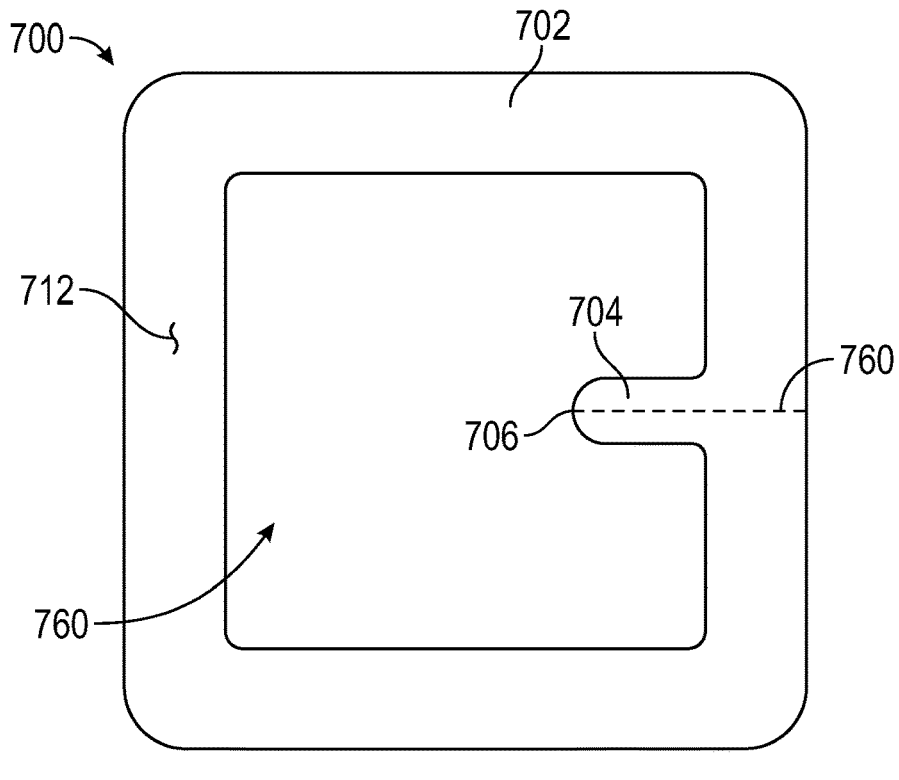
FIG. 11 is a top view of an exemplary embodiment of an overlay adhesive component suitable for use with an apparatus that is adherable to a user's skin.
Figure 12:
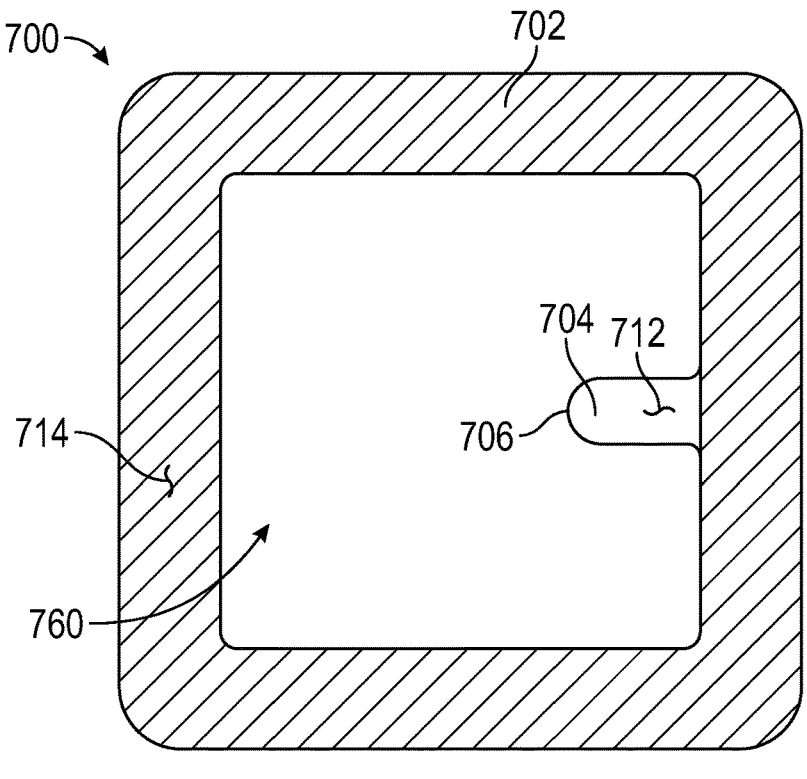
FIG. 12 is a bottom view of the overlay adhesive component.
Figure 13:
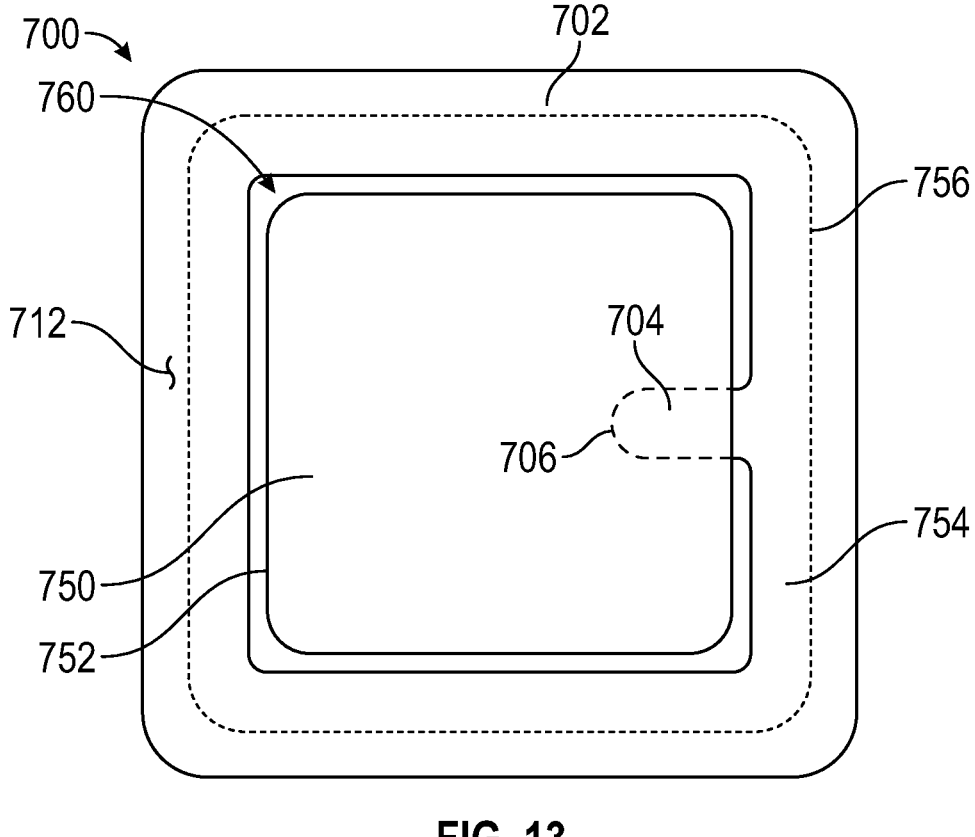
FIG. 13 is a top view of an exemplary embodiment of an assembly that includes an apparatus adhered to a user's skin and the overlay adhesive component.

A skin-affixable apparatus of the type described herein can be further secured to the user's skin by way of an overlay adhesive component that covers at least a portion of the skin adhesive component. In this regard, FIG. 11 is a top view of an exemplary embodiment of an overlay adhesive component 700 suitable for use with an apparatus that is adherable to a user's skin, FIG. 12 is a bottom view of the overlay adhesive component 700, and FIG. 13 is a top view of an exemplary embodiment of an assembly that includes an apparatus adhered to a user's skin using the overlay adhesive component 700. The overlay adhesive component 700 is shaped, sized, and configured to cover at least a portion of the skin adhesive component when adhered to the user's skin. The overlay adhesive component 700 protects the underlying skin adhesive component, which helps keep the durable component affixed to the user's skin for the intended period of wear. As described above with reference to the skin adhesive component 104 (see FIG. 1 and FIG. 2), the overlay adhesive component 700 can be fabricated as a multilayer element having an upper backing material, a lower adhesive material on the backing material, and a removable liner that covers the adhesive material during manufacturing and assembly. Depending on the particular application and use case, the liner can be removed and discarded before final assembly and packaging occurs, or it can remain in place until removed by the user prior to deployment onto the skin.

Referring to FIG. 11 and FIG. 12, the overlay adhesive component 700 includes a protective adhesive region 702 and a pull tab 704 coupled to or integrated with the protective adhesive region 702. The protective adhesive region 702 is shaped and sized for compatibility with a skin adhesive component of an apparatus that is adherable to a user's skin. More specifically, the protective adhesive region 702 is shaped, sized, and configured to cover at least an outer edge of the skin adhesive component. The pull tab 704 is shaped and sized to facilitate removal of the overlay adhesive component 700. To this end, a free end 706 of the pull tab 704 can be tucked between the durable component and the skin adhesive component that affixes the durable component to the user's skin.

In certain embodiments, the pull tab 704 is non-adhesive to make it easier to untuck and grasp. As mentioned above, the overlay adhesive component 700 includes a backing material 712 and adhesive material 714 on the backing material 712. In the top view of FIG. 11, only the backing material 712 is visible. The adhesive material 714 is depicted as a shaded area in the bottom view of FIG. 12. For the illustrated embodiment, the pull tab 704 is void of the adhesive material 714. In other words, the pull tab 704 is realized as a shaped feature of the backing material 712 with no underlying adhesive material 714.

FIG. 13 depicts the overlay adhesive component 700 as deployed with an apparatus affixed to the user's skin. The overlay adhesive component 700 can be provided as a distinct and separate component that can be applied by the user. Alternatively, the overlay adhesive component 700 can be provided as part of an assembly that includes the wearable apparatus and the skin adhesive component. In this regard, the assembly may be loaded into a suitably configured insertion device or mechanism that is packaged for consumer use.

The apparatus includes a durable component 750 having an outer periphery 752. The apparatus also includes a skin adhesive component 754 attached to the durable component 750. The skin adhesive component 754 includes adhesive material for securing to the user's skin (as described in detail above). The outer edge 756 of the skin adhesive component 754 is depicted as a dashed outline because it resides underneath the overlay adhesive component 700. The illustrated embodiment of the overlay adhesive component 700 is generally ring shaped to define a central opening 760 that accommodates passage of the housing of the durable component 750 during deployment of the overlay adhesive component 700. As shown in FIG. 13, the central opening 760 is shaped and sized to fit the outer periphery 752 of the durable component 750. The ring defined by the overlay adhesive component 700 completely overlaps and covers the outer edge 756 of the skin adhesive component 754.

As shown in FIG. 13, the free end 706 of the pull tab 704 can be tucked under the housing of the durable component 750. This prevents accidental lifting of the pull tab 704, and provides a clean appearance. Referring to FIG. 2, the free end 706 of the pull tab 704 can extend under the durable component 750 and fit into space that is not occupied by the adhesive element 140. Thus, the free end of the pull tab can reside between the housing and the skin adhesive component when the overlay adhesive component 700 is deployed overlying the skin adhesive component. In certain embodiments, the durable component 750 may be provided with one or more features or elements (e.g., a slot, a cutout, a pocket, or a tab) designed to accommodate or "store" the pull tab 704 until it is ready for use.

As an optional feature, the overlay adhesive component 700 can be perforated, slit, or pre-cut at one or more locations to facilitate removal. For example, FIG. 11 shows a perforated line 760 that runs along the longitudinal axis of the pull tab 704 and extends to the outer edge of the overlay adhesive component 700. The overlay adhesive component 700 can be separated along the perforated line 760 and peeled away from the skin using a circular motion.

A "refreshable" multi-part skin adhesive component of the type described above with reference to FIGS. 1-10 may also include a pull tab (similar to the pull tab 704 provided with the overlay adhesive component 700). More specifically, a tuckable pull tab can be shaped, sized, and positioned to facilitate removal of a region, section, or segment of a skin adhesive component. For example, a pull tab can be integrated into an outer removable segment of a skin adhesive component to make it easier to separate and remove the outer segment from the inner section of the skin adhesive component. Such a pull tab can be utilized with any of the variations described herein.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An apparatus adherable to a user's skin, the apparatus comprising:

a durable component comprising a housing having a periphery; and a skin adhesive component coupled to the durable component; said skin adhesive component being adapted to secure the durable component to the user's skin, the skin adhesive component comprising:

a first region; and a second region removably attached to the first region along a boundary, the second region having an exposed outer portion;

wherein the periphery completely surrounds the boundary in a top view; and wherein the exposed outer portion completely surrounds the periphery in the top view; and wherein the first region completely resides within a footprint of the durable component such that the first region is protected from exposure or peeling by the durable component.

2. The apparatus of claim 1, wherein the housing comprises a base section coupled to the skin adhesive component, and the periphery of the housing is defined by the base section.

3. The apparatus of claim 1, wherein the housing comprises a sidewall section, and the periphery of the housing is defined by the sidewall section.

4. The apparatus of claim 1, wherein the skin adhesive component comprises perforations formed therein to define the boundary.

5. The apparatus of claim 1, wherein the skin adhesive component is cut, slit, scored, punctured, or broken in a layout to define the boundary.

6. The apparatus of claim 1, wherein the skin adhesive component comprises a mechanically weakened or compromised outline to define the boundary.

7. The apparatus of claim 1, wherein the second region of the skin adhesive component comprises a plurality of individually removable segments.

8. The apparatus of claim 1, wherein the skin adhesive component further comprises a third region removably attached to the second region along a second boundary.

9. The apparatus of claim 1, wherein the boundary is spiral shaped.

10. The apparatus of claim 1, wherein the skin adhesive component further comprises a pull tab coupled to the second region, the pull tab shaped and sized to facilitate removal of the second region, wherein a free end of the pull tab is tucked under the housing of the durable component.

11. The apparatus of claim 1, further comprising an overlay adhesive component to cover at least a portion of the skin adhesive component when adhered to the user's skin, the overlay adhesive component comprising:

a protective adhesive region shaped and sized for compatibility with the skin adhesive component to cover an outer edge of the skin adhesive component; and a pull tab coupled to the protective adhesive region, the pull tab shaped and sized to facilitate removal of the overlay adhesive component, wherein a free end of the pull tab is tucked between the housing and the skin adhesive component when the overlay adhesive component is deployed.

12. The apparatus of claim 11, wherein the protective adhesive region is ring shaped to define a central opening that accommodates passage of the housing of the durable component during deployment of the overlay adhesive component.

13. The apparatus of claim 11, wherein the pull tab is non-adhesive.

14. The apparatus of claim 13, wherein:

the overlay adhesive component comprises a backing material and an adhesive material on the backing material; and the pull tab is void of the adhesive material.

15. An apparatus adherable to a user's skin, the apparatus comprising:

a durable component having a periphery defining a footprint of the durable component; and a skin adhesive component coupled to the durable component to; said skin adhesive component being adapted to the durable component to the user's skin, the skin adhesive component comprising:

a first region; and a second region removably attached to the first region along a boundary, the second region having an exposed outer portion;

wherein the periphery completely surrounds the boundary in a top view; and wherein the exposed outer portion completely surrounds the periphery in the top view; and wherein the first region completely resides within a footprint of the durable component such that the first region is protected from exposure or peeling by the durable component.

16. The apparatus of claim 15, wherein the skin adhesive component comprises perforations formed along the boundary between the first region and the second region.

17. The apparatus of claim 15, further comprising an overlay adhesive component to cover at least a portion of the skin adhesive component when adhered to the user's skin, the overlay adhesive component comprising:

a protective adhesive region shaped and sized for compatibility with the skin adhesive component to cover an outer edge of the skin adhesive component; and a pull tab coupled to the protective adhesive region, the pull tab shaped and sized to facilitate removal of the overlay adhesive component, wherein a free end of the pull tab is tucked between the durable component and the skin adhesive component when the overlay adhesive component is deployed.

18. The apparatus of claim 17, wherein the pull tab is non-adhesive.

19. The apparatus of claim 18, wherein:

the overlay adhesive component comprises a backing material and an adhesive material on the backing material; and the pull tab is void of the adhesive material.

20. The apparatus of claim 17, wherein the protective adhesive region is ring shaped to define a central opening that accommodates passage of the durable component during deployment of the overlay adhesive component.

* * * * *